United States Patent [19]

Nakajima et al.

[11] Patent Number: 4,918,107

[45] Date of Patent: Apr. 17, 1990

[54] GLUTAMATE RECEPTOR INHIBITOR AND INSECTICIDAL COMPOSITION

[75] Inventors: Terumi Nakajima; Nobufumi Kawai; Koichi Shudo, all of Tokyo; Tetsuo Shiba, Osaka, all of Japan

[73] Assignees: Tsumura & Co.; Tokyo Metropolitan Institute for Neurosciences, both of Tokyo; Takeda Chemical Industries, Ltd., Osaka, all of Japan

[21] Appl. No.: 202,491

[22] Filed: Jun. 6, 1988

[30] Foreign Application Priority Data

Jun. 10, 1987 [JP] Japan .................. 62-145666
Apr. 28, 1988 [JP] Japan .................. 63-107157

[51] Int. Cl.$^4$ .................. C07C 103/30; A01N 37/18
[52] U.S. Cl. ..................... 514/616; 564/153
[58] Field of Search .................. 514/616; 564/153

[56] References Cited

PUBLICATIONS

Adams et al., "Structures and Biological Activities of Three Synaptic Antagonists, etc.", CA 108, 17509u (1988).
Aramaki et al., "Solution and Characterization of Spider Toxin, JSTX and NSTX, etc.", CA 109, 50385u (1988).

Primary Examiner—Richard L. Raymond
Assistant Examiner—Peter G. O'Sullivan
Attorney, Agent, or Firm—Antonelli, Terry & Wands

[57] ABSTRACT

A compound of the formula

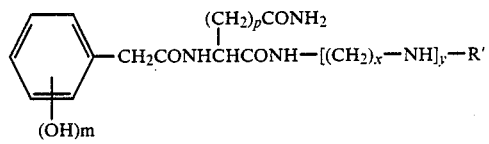

wherein R' is hydrogen atom or an alkyl group, m is an integer of 1 to 3, p is 1 or 2, x is an integer of 2 to 6, and y is an integer of 1 to 3, or a salt thereof, which has glutamate receptor inhibitor activity, a process for preparing the same and an insecticidal composition containing the same are provided.

14 Claims, No Drawings

GLUTAMATE RECEPTOR INHIBITOR AND INSECTICIDAL COMPOSITION

BACKGROUND OF THE INVENTION

1. Field of the Invention

The present invention relates to a novel compound having a glutamate receptor inhibiting activity, a process for producing the same and an insecticidal composition containing the same.

2. Description of the Prior Art

A chemical substance which paralyzes the nerve of arthropods such as insects has been isolated from spiders and structure thereof has been elucidated to some extent and it has been confirmed that the nerve paralyzing action is due to the glutamate receptor inhibiting action. "Proceedings of the Japan Academy", 62 Ser. B, 359(1986) discloses $N^1$-(2,4-dihydroxyphenylacetylasparaginyl)-$N^5$-(alginylcadaverino-$\beta$-alanyl) cadaverine and the like and Chemical Abstracts, 105:186106d(1986) discloses (2,4-dihydroxyphenylacetylasparaginyl)-polyamine-(alginyl) [the polyamine is $-NH(CH_2)_3NH(CH_2)_3NH(CH_2)_5NH-$].

Problems come up what is the essence of the action of the glutamate receptor substances including the above chemical substances and what chemical modification is possible.

The inventors synthesized compounds having a part of the structure of the above chemical substances and the above chemical substances which were chemically modified and studied their glutamate receptor inhibiting action to find that the partial structure of the chemical substances alone develops the glutamate receptor inhibiting action. As a result of further investigation, the present inventon has been accomplished.

SUMMARY OF THE INVENTION

The present invention includes:
(1) a compound of the formula:

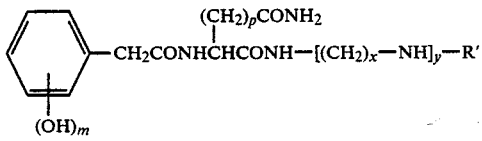

wherein R' is hydrogen atom or an alkyl group, m is an integer of 1 to 3, p is 1 or 2, x is an integer of 2 to 6 and y is an integer of 1 to 3, or a salt thereof, [referred to as "compound [I]" hereinafter], (2) a process for producing the compound [I] which comprises allowing a carboxylic acid of the formula:

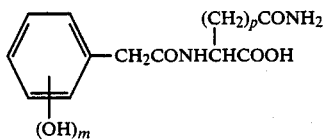

[wherein the symbols p and m are the same as defined above], or a salt or a reactive derivative thereof to react with an amino compound of the formula: $NH_2-[(CH_2)_x-NH]_y-R'$, wherein the symbols x, y and R' are the same as defined above, or a salt thereof and, if necessary, eliminating a protecting group, and (3) an insecticidal composition containing the compound [I].

DETAILED DESCRIPTION OF THE PREFERRED EMBODIMENTS

In the compound [I], R' is hydrogen atom or an alkyl group which is defined hereinafter as the alkyl* group. Symbol m is an integer of 1 to 3, i.e., 1, 2 or 3. The substituent hydroxyl group may be located at any position of 2, 3, 4, 5 and 6. The symbol p is 1 or 2. The symbols x and y are an integer of 2 to 6 and an integer of 1 to 3, respectively. Accordingly, in the compound [I], $-[(CH_2)_x-NH]_y$ is $-(CH_2)_{x1}-NH-$, $-(CH_2)_{x2}-NH-(NH_2)_{x3}-NH-$ or $-(CH_2)_{x4}-NH-(CH_2)_{x5}-NH-(CH_2)_{x6}-NH-$, when y is 1, 2 or 3, respectively, wherein x1–x6 each is an integer of 2–6.

A compound [I] or a salt thereof may also be rewritten as follows:

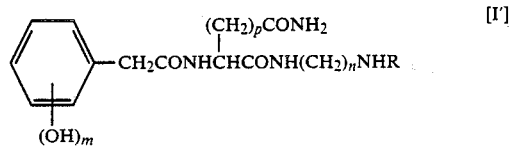

wherein R is hydrogen atom, an alkyl* group, an aminoalkyl group, an (alkyl*amino)alkyl group, an (aminoalkylamino)alkyl group or an {(alkyl*amino)alkylamino} alkyl group, m is an integer of 1 to 3, n is an integer of 2 to 6 and p is 1 or 2.

In the formula [I'], alkyl* group is preferably a straight chain or branched chain alkyl group having 1 to 10 carbon atoms (hereinafter referred to as a "$C_{1-10}$ alkyl group"), more preferably a straight chain or branched chain alkyl having 1 to 6 carbon atoms (hereinafter referred to as a "$C_{1-6}$ alkyl group"). The alkyl* group or a $C_{1-6}$ alkyl group includes, for example, methyl, ethyl, propyl, isopropyl, butyl, isobutyl, sec-butyl, tert-butyl, pentyl, isopentyl, 2-methylbutyl, 1-methylbutyl, 1,2-dimethylpropyl, 1,1-dimethylpropyl, neopentyl, 1-ethylpropyl, hexyl isohexyl, 4-methylpentyl, 3-methylpentyl, 2-methylpentyl, 1-methylpentyl, 2,3-dimethylbutyl, 1,3-dimethylbutyl, 1,2-dimethylbutyl, 3,3-dimethylbutyl, 2,2-dimethylbutyl, 1,1-dimethylbutyl, 1,2,2-trimethylpropyl, 1,1,2-trimethylpropyl, 2-ethylbutyl, 1-ethylbutyl, 1-ethyl-2-methylpropyl and 1-ethyl-1-methylpropyl.

The alkyl group of the aminoalkyl group as R means a straight chain alkyl group of 2–6 carbon atoms [referred to as a "$C_{2-6}$ alkyl group" hereinafter]. The amino group is substituted at $\omega$-position of the alkyl group. Examples of the aminoalkyl group or amino-$C_{2-6}$ alkyl group are 2-aminoethyl, 3-aminopropyl, 4-aminobutyl, 5-aminopentyl and 6-aminohexyl.

The (alkyl*amino)alkyl group as R means a ($C_{1-6}$ alkylamino)-$C_{2-6}$ alkyl group. The (alkyl*amino)alkyl group or ($C_{1-6}$ alkylamino)-$C_{2-6}$ alkyl group includes, for example, 2-(methylamino)ethyl, 2-(ethylamino)ethyl, 2-(isopropylamino)ethyl, 2-(hexylamino)ethyl, 3-(methylamino)propyl, 3-(ethylamino)propyl, 3-(isopropylamino)propyl, 3-(hexylamino)propyl, 4-(methylamino)butyl, 4-(ethylamino)butyl, 4-(isopropylamino)butyl, 4-(hexylamino)butyl, 5-(methylamino)pentyl, 5-(ethylamino)pentyl, 5-(isopropylamino)pentyl, 5-(hexylamino)pentyl, 6-(methylamino)hexyl, 6-(ethylamino)hexyl, 6-(isopropylamino)hexyl and 6-(hexylamino)hexyl.

The (aminoalkylamino)alkyl group as R means an (amino-$C_{2-6}$ alkylamino)-$C_{2-6}$ alkyl group. The amino group is substituted at ω-position of the alkyl group. The (aminoalkylamio)alkyl group or (amino-$C_{2-6}$ alkylamino)-$C_{2-6}$ alkyl group includes, for example,
2-{(2-aminoethyl)amino}ethyl,
3-{(2-aminoethyl)amino}propyl,
4-{(2-aminoethyl)amino}butyl,
5-{(2-aminoethyl)amino}pentyl,
6-{(2-aminoethyl)amino}hexyl,
2-{(3-aminopropyl)amino}ethyl
3-{(3-aminopropyl)amino}propyl,
4-{(3-aminopropyl)amino}butyl,
5-{(3-aminopropyl)amino}pentyl,
6-{(3-aminopropyl)amino}hexyl,
2-{(4-aminobutyl)amino}ethyl,
3-{(4-aminobutyl)amino}propyl,
4-{(4-aminobutyl)amino}butyl,
5-{(4-aminobutyl)amino}pentyl,
6-{(4-aminobutyl)amino}hexyl,
2-{(5-aminopentyl)amino}ethyl,
3-{(5-aminopentyl)amino}propyl,
4-{(5-aminopentyl)amino}butyl,
5-{(5-aminopentyl)amino}pentyl,
6-{(5-aminopentyl)amino}hexyl,
2-{(6-aminohexyl)amino}ethyl,
3-{(6-aminohexyl)amino}propyl,
4-{(6-aminohexyl)amino}butyl,
5-{(6-aminohexyl)amino}pentyl and
6-{(6-aminohexyl)amino}hexyl.

The {(alkyl*amino)alkylamino}alkyl group as R means a {($C_{1-6}$ alkylamino)-$C_{2-6}$ alkylamino}-$C_{2-6}$ alkyl group. The {(alkyl*amino)alkylamino}alkyl group or {($C_{1-6}$ alkylamino)-$C_{2-6}$ alkylamino}-$C_{2-6}$ alkyl group includes, for example,
2-{{2-(methylamino)ethyl}amino}ethyl,
2-{{2-(ethylamino)ethyl}amino ethyl,
2-{{2-(isopropylamino)ethyl}amino}ethyl,
2-{{2-(hexylamino)ethyl}amino}ethyl,
3-{{2-(methylamino)ethyl}amino}propyl,
3-{{2-(ethylamino)ethyl}amino}propyl,
3-{{2-(isopropylamino)ethyl}amino}propyl,
3-{{2-(hexylamino)ethyl}amino}propyl,
4-{{2-(methylamino)ethyl}amino}butyl,
4-{{2-(ethylamino)ethyl}amino}butyl,
4-{{2-(isopropylamino)ethyl}amino}butyl,
4-{{2-(hexylamino)ethyl}amino}butyl,
5-{{2-(methylamino)ethyl}amino}pentyl,
5-{{2-(ethylamino)ethyl}amino}pentyl,
5-{{2-(isopropylamino)ethyl}amino}pentyl,
5-{{2-(hexylamino)ethyl}amino}pentyl,
6-{{2-(methylamino)ethyl}amino}hexyl,
6-{{2-(ethylamino)ethyl}amino}hexyl,
6-{{2-(isopropylamino)ethyl}amino}hexyl,
6-{{2-(hexylamino)ethyl}amino}hexyl,
2-{{3-(methylamino)propyl}amino}ethyl,
2-{{3-(ethylamino)propyl}amino}ethyl,
2-{{3-(isopropylamino)propyl}amino}ethyl,
2-{{3-(hexylamino)propyl}amino}ethyl,
3-{{3-(methylamino)propyl}amino}propyl,
3-{{3-(ethylamino)propyl}amino}propyl,
3-{{3-(isopropylamino)propyl}amino}propyl,
3-{{3-hexylamino)propyl}amino}propyl,
4-{{3-(methylamino)propyl}amino}butyl,
4-{{3-(ethylamino)propyl}amino}butyl,
4-{{3-(isopropylamino)propyl}amino}butyl,
4-{{3-(hexylamino)propyl}amino}butyl,
5-{{3-(methylamino)propyl}amino}pentyl,
5-{{3-(ethylamino)propyl}amino}pentyl,
5-{{3-(isopropylamino)propyl}amino}pentyl,
5-{{3-(hexylamino)propyl}amino}pentyl,
6-{{3-(methylamino)propyl}amino}hexyl,
6-{{3-(ethylamino)propyl}amino}hexyl,
6-{{3-(isopropylamino)propyl}amino}hexyl,
6-{{3-(hexylamino)propyl}amino}hexyl,
2-{{4-(methylamino)butyl}amino}ethyl,
2-{{4-(ethylamino)butyl}amino}ethyl,
2-{{4-(isopropylamino)butyl}amino}ethyl,
2-{{4-(hexylamino)butyl}amino}ethyl,
3-{{4-(methylamino)butyl}amino}propyl,
3-{{4-(ethylamino)butyl}amino}propyl,
3-{{4-(isopropylamino)butyl}amino}propyl,
3-{{4-(hexylamino)butyl}amino}propyl,
4-{{4-(methylamino)butyl}amino}butyl,
4-{{4-(ethylamino)butyl}amino}butyl,
4-{{4-(isopropylamino)butyl}amino}butyl,
4-{{4-(hexylamino)butyl}amino}butyl,
5-{{4-(methylamino)butyl}amino}pentyl,
5-{{4-(ethylamino)butyl}amino}pentyl,
5-{{4-(isopropylamino)butyl}amino}pentyl,
5-{{4-(hexylamino)butyl}amino}pentyl,
6-{{4-(methylamino)butyl}amino}hexyl,
6-{{4-(ethylamino)butyl}amino}hexyl,
6-{{4-(isopropylamino)butyl}amino}hexyl,
6-{{4-(hexylamino)butyl}amino}hexyl,
2-{{5-(methylamino)pentyl}amino}ethyl,
2-{{5-(ethylamino)pentyl}amino}ethyl,
2-{{5-(isopropylamino)pentyl}amino}ethyl,
2-{{5-(hexylamino)pentyl}amino}ethyl,
3-{{5-(methylamino)pentyl}amino}propyl,
3-{{5-(ethylamino)pentyl}amino}propyl,
3-{{5-(isopropylamino)pentyl{amino{propyl,
3-{{5-(hexylamino)pentyl}amino}propyl,
4-{{5-(methylamino)pentyl}amino}butyl,
4-{{5-(ethylamino)pentyl}amino}butyl,
4-{{5-(isopropylamino)pentyl}amino}butyl,
4-{{5-(hexylamino)pentyl}amino}butyl,
5-{{5-(methylamino)pentyl}amino}pentyl,
5-{{5-(ethylamino)pentyl}amino}pentyl,
5-{{5-(isopropylamino)pentyl}amino}pentyl,
5-{{5-(hexylamino)pentyl}amino}pentyl,
6-{{5-(methylamino)pentyl}amino}hexyl,
6-{{5-(ethylamino)pentyl}amino}hexyl,
6-{{5-(isopropylamino)pentyl}amino}hexyl,
6-{{5-(hexylamino)pentyl}amino}hexyl,
2-{{6-(methylamino)hexyl}amino}ethyl,
2-{{6-(ethylamino)hexyl}amino}ethyl,
2-{{6-(isopropylamino)hexyl}amino}ethyl,
2-{{6-(hexylamino)hexyl}amino}ethyl,
3-{{6-(methylamino)hexyl}amino}propyl,
3-{{6-(ethylamino)hexyl}amino}propyl,
3-{{6-(isopropylamino)hexyl}amino}propyl,
3-{{6-(hexylamino)hexyl}amino}propyl,
4-{{6-(methylamino)hexyl}amino}butyl,
4-{{6-(ethylamino)hexyl}amino}butyl,
4-{{6-(isopropylamino)hexyl}amino}butyl,
4-{{6-(hexylamino)hexyl}amino}butyl,
5-{{6-(methylamino)hexyl}amino}pentyl,
5-{{6-(ethylamino)hexyl}amino}pentyl,
5-{{6-(isopropylamino)hexyl}amino}pentyl,
5-{{6-(hexylamino)hexyl}amino}pentyl,
6-{{6-(methylamino)hexyl}amino}hexyl,
6-{{6-(ethylamino)hexyl}amino}hexyl,
6-{{6-(isopropylamino)hexyl}amino}hexyl and
6-{{6-(hexylamino)hexyl}amino}hexyl.

Examples of the compound [I] or [I'] (including salt thereof) are enumerated in the following Table 1.

TABLE 1

| Compound No. | Chemical structure |
|---|---|
| 1 | HO—C6H3(OH)—CH2CONHCH(CH2CONH2)CONH(CH2)3NH2 |
| 2 | HO—C6H3(OH)—CH2CONHCH(CH2CONH2)CONH(CH2)4NH2 |
| 3 | HO—C6H3(OH)—CH2CONHCH(CH2CONH2)CONH(CH2)5NH2 |
| 4 | HO—C6H3(OH)—CH2CONHCH(CH2CONH2)CONH(CH2)3NHC2H5 |
| 5 | HO—C6H4—CH2CONHCH(CH2CONH2)CONH(CH2)4NHC2H5 |
| 6 | HO—C6H3(OH)—CH2CONHCH(CH2CONH2)CONH(CH2)5NHC2H5 |
| 7 | HO—C6H3(OH)—CH2CONHCH(CH2CH2CONH2)CONH(CH2)3NH(CH2)3NH2 |
| 8 | HO—C6H3(OH)—CH2CONHCH(CH2CH2CONH2)CONH(CH2)3NH(CH2)4NH2 |
| 9 | HO—C6H3(OH)—CH2CONHCH(CH2CH2CONH2)CONH(CH2)3NH(CH2)5NH2 |
| 10 | HO—C6H3(OH)—CH2CONHCH(CH2CONH2)CONH(CH2)4NH(CH2)3NH2 |
| 11 | HO—C6H4—CH2CONHCH(CH2CONH2)CONH(CH2)4NH(CH2)4NH2 |

TABLE 1-continued

| Compound No. | Chemical structure |
|---|---|
| 12 | 2,4,6-trihydroxyphenyl-CH₂CONHCH(CH₂CONH₂)CONH(CH₂)₄NH(CH₂)₅NH₂ |
| 13 | 2,4-dihydroxyphenyl-CH₂CONHCH(CH₂CONH₂)CONH(CH₂)₅NH(CH₂)₃NH₂ |
| 14 | 4-hydroxyphenyl-CH₂CONHCH(CH₂CONH₂)CONH(CH₂)₅NH(CH₂)₄NH₂ |
| 15 | 2,4,6-trihydroxyphenyl-CH₂CONHCH(CH₂CONH₂)CONH(CH₂)₅NH(CH₂)₅NH₂ |
| 16 | 2,4-dihydroxyphenyl-CH₂CONHCH(CH₂CONH₂)CONH(CH₂)₃NH(CH₂)₃NHC₂H₅ |
| 17 | 2,4-dihydroxyphenyl-CH₂CONHCH(CH₂CONH₂)CONH(CH₂)₃NH(CH₂)₄NHC₂H₅ |
| 18 | 2,4-dihydroxyphenyl-CH₂CONHCH(CH₂CONH₂)CONH(CH₂)₃NH(CH₂)₅NHC₂H₅ |
| 19 | 2,4-dihydroxyphenyl-CH₂CONHCH(CH₂CH₂CONH₂)CONH(CH₂)₄NH(CH₂)₃NHC₂H₅ |
| 20 | 4-hydroxyphenyl-CH₂CONHCH(CH₂CH₂CONH₂)CONH(CH₂)₄NH(CH₂)₄NHC₂H₅ |
| 21 | 2,4,6-trihydroxyphenyl-CH₂CONHCH(CH₂CH₂CONH₂)CONH(CH₂)₄NH(CH₂)₅NHC₂H₅ |

TABLE 1-continued

| Compound No. | Chemical structure |
|---|---|
| 22 | 2,4-(HO)₂C₆H₃-CH₂CONHCH(CH₂CONH₂)CONH(CH₂)₅NH(CH₂)₃NHC₂H₅ |
| 23 | 2,4-(HO)₂C₆H₃-CH₂CONHCH(CH₂CONH₂)CONH(CH₂)₅NH(CH₂)₄NHC₂H₅ |
| 24 | 2,4-(HO)₂C₆H₃-CH₂CONHCH(CH₂CONH₂)CONH(CH₂)₅NH(CH₂)₅NHC₂H₅ |
| 25 | 2,4-(HO)₂C₆H₃-CH₂CONHCH(CH₂CONH₂)CONH(CH₂)₃NH(CH₂)₃NH(CH₂)₃NH₂ |
| 26 | 4-HOC₆H₄-CH₂CONHCH(CH₂CONH₂)CONH(CH₂)₃NH(CH₂)₃NH(CH₂)₄NH₂ |
| 27 | 2,4,6-(HO)₃C₆H₂-CH₂CONHCH(CH₂CONH₂)CONH(CH₂)₃NH(CH₂)₃NH(CH₂)₅NH₂ |
| 28 | 2,4-(HO)₂C₆H₃-CH₂CONHCH(CH₂CONH₂)CONH(CH₂)₃NH(CH₂)₄NH(CH₂)₃NH₂ |
| 29 | 2,4-(HO)₂C₆H₃-CH₂CONHCH(CH₂CONH₂)CONH(CH₂)₃NH(CH₂)₄NH(CH₂)₄NH₂ |
| 30 | 2,4-(HO)₂C₆H₃-CH₂CONHCH(CH₂CONH₂)CONH(CH₂)₃NH(CH₂)₄NH(CH₂)₅NH₂ |
| 31 | 2,4-(HO)₂C₆H₃-CH₂CONHCH(CH₂CONH₂)CONH(CH₂)₃NH(CH₂)₅NH(CH₂)₃NH₂ |
| 32 | 4-HOC₆H₄-CH₂CONHCH(CH₂CONH₂)CONH(CH₂)₃NH(CH₂)₅NH(CH₂)₄NH₂ |

TABLE 1-continued

| Compound No. | Chemical structure |
|---|---|
| 33 | 2,4-dihydroxyphenyl-CH₂CONHCH(CH₂CONH₂)CONH(CH₂)₃NH(CH₂)₅NH(CH₂)₅NH₂ |
| 34 | 2,4-dihydroxyphenyl-CH₂CONHCH(CH₂CH₂CONH₂)CONH(CH₂)₄NH(CH₂)₃NH(CH₂)₃NH₂ |
| 35 | 2,4-dihydroxyphenyl-CH₂CONHCH(CH₂CH₂CONH₂)CONH(CH₂)₄NH(CH₂)₃NH(CH₂)₄NH₂ |
| 36 | 2,4-dihydroxyphenyl-CH₂CONHCH(CH₂CH₂CONH₂)CONH(CH₂)₄NH(CH₂)₃NH(CH₂)₅NH₂ |
| 37 | 2-hydroxyphenyl-CH₂CONHCH(CH₂CONH₂)CONH(CH₂)₄NH(CH₂)₄NH(CH₂)₃NH₂ |
| 38 | 2-hydroxyphenyl-CH₂CONHCH(CH₂CONH₂)CONH(CH₂)₄NH(CH₂)₄NH(CH₂)₄NH₂ |
| 39 | 2-hydroxyphenyl-CH₂CONHCH(CH₂CONH₂)CONH(CH₂)₄NH(CH₂)₄NH(CH₂)₅NH₂ |
| 40 | 2,4-dihydroxyphenyl-CH₂CONHCH(CH₂CONH₂)CONH(CH₂)₄NH(CH₂)₅NH(CH₂)₃NH₂ |
| 41 | 2,4-dihydroxyphenyl-CH₂CONHCH(CH₂CONH₂)CONH(CH₂)₄NH(CH₂)₅NH(CH₂)₄NH₂ |
| 42 | 2,4-dihydroxyphenyl-CH₂CONHCH(CH₂CONH₂)CONH(CH₂)₄NH(CH₂)₅NH(CH₂)₅NH₂ |
| 43 | 2,4-dihydroxyphenyl-CH₂CONHCH(CH₂CONH₂)CONH(CH₂)₅NH(CH₂)₃NH(CH₂)₃NH₂ |

TABLE 1-continued

| Compound No. | Chemical structure |
|---|---|
| 44 | HO—C6H4—CH2CONHCH(CH2CONH2)CONH(CH2)5NH(CH2)3NH(CH2)4NH2 |
| 45 | (2,4,6-triOH)C6H2—CH2CONHCH(CH2CONH2)CONH(CH2)5NH(CH2)3NH(CH2)5NH2 |
| 46 | (2,4-diOH)C6H3—CH2CONHCH(CH2CONH2)CONH(CH2)5NH(CH2)4NH(CH2)3NH2 |
| 47 | (2,4-diOH)C6H3—CH2CONHCH(CH2CONH2)CONH(CH2)5NH(CH2)4NH(CH2)4NH2 |
| 48 | (2,4-diOH)C6H3—CH2CONHCH(CH2CONH2)CONH(CH2)5NH(CH2)4NH(CH2)5NH2 |
| 49 | (2,4-diOH)C6H3—CH2CONHCH(CH2CH2CONH2)CONH(CH2)5NH(CH2)5NH(CH2)3NH2 |
| 50 | (2,4-diOH)C6H3—CH2CONHCH(CH2CH2CONH2)CONH(CH2)5NH(CH2)5NH(CH2)4NH2 |
| 51 | (2,4-diOH)C6H3—CH2CONHCH(CH2CH2CONH2)CONH(CH2)5NH(CH2)5NH(CH2)5NH2 |
| 52 | (2-OH)C6H4—CH2CONHCH(CH2CH2CONH2)CONH(CH2)3NH(CH2)3NH(CH2)3NHC2H5 |
| 53 | (2-OH)C6H4—CH2CONHCH(CH2CH2CONH2)CONH(CH2)3NH(CH2)3NH(CH2)4NHC2H5 |
| 54 | (2-OH)C6H4—CH2CONHCH(CH2CH2CONH2)CONH(CH2)3NH(CH2)3NH(CH2)5NHC2H5 |

TABLE 1-continued

| Compound No. | Chemical structure |
|---|---|
| 55 | 2,6-(OH)₂C₆H₃—CH₂CONHCH(CH₂CONH₂)CONH(CH₂)₃NH(CH₂)₄NH(CH₂)₃NHC₂H₅ |
| 56 | 2,6-(OH)₂C₆H₃—CH₂CONHCH(CH₂CONH₂)CONH(CH₂)₃NH(CH₂)₄NH(CH₂)₄NHC₂H₅ |
| 57 | 2,6-(OH)₂C₆H₃—CH₂CONHCH(CH₂CONH₂)CONH(CH₂)₃NH(CH₂)₄NH(CH₂)₅NHC₂H₅ |
| 58 | 2,4-(OH)₂C₆H₃—CH₂CONHCH(CH₂CH₂CONH₂)CONH(CH₂)₃NH(CH₂)₅NH(CH₂)₃NHC₂H₅ |
| 59 | 2,4-(OH)₂C₆H₃—CH₂CONHCH(CH₂CH₂CONH₂)CONH(CH₂)₃NH(CH₂)₅NH(CH₂)₄NHC₂H₅ |
| 60 | 2,4-(OH)₂C₆H₃—CH₂CONHCH(CH₂CH₂CONH₂)CONH(CH₂)₃NH(CH₂)₅NH(CH₂)₅NHC₂H₅ |
| 61 | 2,4-(OH)₂C₆H₃—CH₂CONHCH(CH₂CONH₂)CONH(CH₂)₄NH(CH₂)₃NH(CH₂)₃NHC₂H₅ |
| 62 | 4-(OH)C₆H₄—CH₂CONHCH(CH₂CONH₂)CONH(CH₂)₄NH(CH₂)₃NH(CH₂)₄NHC₂H₅ |
| 63 | 2,4,6-(OH)₃C₆H₂—CH₂CONHCH(CH₂CONH₂)CONH(CH₂)₄NH(CH₂)₃NH(CH₂)₅NHC₂H₅ |
| 64 | 2,4-(OH)₂C₆H₃—CH₂CONHCH(CH₂CH₂CONH₂)CONH(CH₂)₄NH(CH₂)₄NH(CH₂)₃NHC₂H₅ |

TABLE 1-continued

| Compound No. | Chemical structure |
|---|---|
| 65 | 2,4-dihydroxyphenyl-CH₂CONHCH(CH₂CH₂CONH₂)CONH(CH₂)₄NH(CH₂)₄NH(CH₂)₄NHC₂H₅ |
| 66 | 2,4-dihydroxyphenyl-CH₂CONHCH(CH₂CH₂CONH₂)CONH(CH₂)₄NH(CH₂)₄NH(CH₂)₅NHC₂H₅ |
| 67 | 3,4-dihydroxyphenyl-CH₂CONHCH(CH₂CONH₂)CONH(CH₂)₄NH(CH₂)₅NH(CH₂)₃NHC₂H₅ |
| 68 | 3,4-dihydroxyphenyl-CH₂CONHCH(CH₂CONH₂)CONH(CH₂)₄NH(CH₂)₅NH(CH₂)₄NHC₂H₅ |
| 69 | 3,4-dihydroxyphenyl-CH₂CONHCH(CH₂CONH₂)CONH(CH₂)₄NH(CH₂)₅NH(CH₂)₅NHC₂H₅ |
| 70 | 2,4-dihydroxyphenyl-CH₂CONHCH(CH₂CH₂CONH₂)CONH(CH₂)₃NH(CH₂)₃NH(CH₂)₃NHC₂H₅ |
| 71 | 2,4-dihydroxyphenyl-CH₂CONHCH(CH₂CH₂CONH₂)CONH(CH₂)₅NH(CH₂)₃NH(CH₂)₄NHC₂H₅ |
| 72 | 2,4-dihydroxyphenyl-CH₂CONHCH(CH₂CH₂CONH₂)CONH(CH₂)₅NH(CH₂)₃NH(CH₂)₅NHC₂H₅ |
| 73 | 2,4-dihydroxyphenyl-CH₂CONHCH(CH₂CH₂CONH₂)CONH(CH₂)₅NH(CH₂)₄NH(CH₂)₃NHC₂H₅ |
| 74 | 4-hydroxyphenyl-CH₂CONHCH(CH₂CH₂CONH₂)CONH(CH₂)₅NH(CH₂)₄NH(CH₂)₄NHC₂H₅ |
| 75 | 2,4,6-trihydroxyphenyl-CH₂CONHCH(CH₂CH₂CONH₂)CONH(CH₂)₅NH(CH₂)₄NH(CH₂)₅NHC₂H₅ |

TABLE 1-continued

| Compound No. | Chemical structure |
|---|---|
| 76 | HO—⟨benzene ring with OH⟩—CH₂CONHCHCONH(CH₂)₅NH(CH₂)₅NH(CH₂)₃NHC₂H₅ with CH₂CONH₂ branch |

Compound 76: 
$$\text{HO-}\underset{(OH)}{\text{C}_6\text{H}_3}\text{-CH}_2\text{CONHCH(CH}_2\text{CONH}_2\text{)CONH(CH}_2)_5\text{NH(CH}_2)_5\text{NH(CH}_2)_3\text{NHC}_2\text{H}_5$$

Compound 77:
$$\text{HO-}\underset{(OH)}{\text{C}_6\text{H}_3}\text{-CH}_2\text{CONHCH(CH}_2\text{CONH}_2\text{)CONH(CH}_2)_5\text{NH(CH}_2)_5\text{NH(CH}_2)_4\text{NHC}_2\text{H}_5$$

Compound 78:
$$\text{HO-}\underset{(OH)}{\text{C}_6\text{H}_3}\text{-CH}_2\text{CONHCH(CH}_2\text{CONH}_2\text{)CONH(CH}_2)_5\text{NH(CH}_2)_5\text{NH(CH}_2)_5\text{NHC}_2\text{H}_5$$

The salt of compound [I] includes salts with inorganic acids or organic acids. Examples of the inorganic acid salts are hydrochlorides, sulfates, carbonates and nitrates. Examples of the organic acid salts are formates, acetates, propionates, oxalates, succinates, benzoates and p-toluenesulfonates. The amino acid constituting the compound [I] may be any of L-form, D-form or DL-form, the L-form being more preferable.

The compound [I] is produced by the following process. That is, the compound [I] is produced by allowing carboxylic acid [II] of the formula:

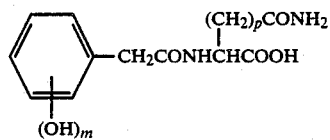

wherein the symbols p and m are the same as above, or a salt or a reactive derivative thereof [referred to as "compound II" hereinafter] to react with compound [III] of the formula: $NH_2[(CH_2)_x-NH]_y-R'$ [the symbols x, y and R' are the same as above] or a salt thereof [referred to as "compound III" hereinafter] and, if necessary eliminating a protecting group (Reaction formula 1).

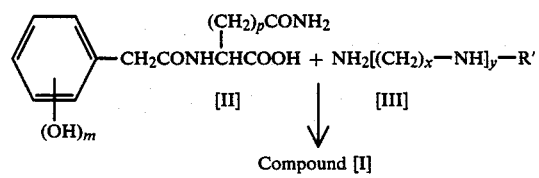

Compound [I]

In the above reaction formula 1, the starting compound [II] may be a salt or reactive derivative thereof and the starting compound [III] may be a salt thereof. The salt of compound [II] includes inorganic base salts or organic base salts of [II]. Examples of the inorganic base salts of [II] are alkali metal salt, e.g., sodium salt and potassium salt and alkaline earth metal salts, e.g., calcium salt. Examples of the organic base salts of [II] are trimethylamine salt, triethylamine salt, tert-butyldimethylamine salt, cyclohexylamine salt, dibenzylmethylamine salt, benzyldimethylamine salt, N,N-dimethylaniline salt, pyridine salt and quinoline salt. The reactive derivative of the starting compound [II] means a reactive derivative at the carboxyl group of the compound. The reactive derivative of compound [II] includes acid halides, acid azides, acid anhydrides, mixed acid anhydrides, active amides, active esters and active thioesters. Examples of acid halides of [II] are acid chloride and acid bromide. Examples of the mixed acid anhydrides are monoalkylcarbonic acid-mixed acid anhydrides, e.g., mixed acid anhydrides of [II] with monomethylcarbonic acid, monoethylcarbonic acid, monoisopropylcarbonic acid, monoisobutylcarbonic acid, mono-tert-butylcarbonic acid, monobenzylcarbonic acid, mono(p-nitrobenzyl)carbonic acid or monoallylcarbonic acid, aliphatic carboxylic acid-mixed acid anhydrides, e.g., mixed acid anhydrides of [II] with acetic acid, thichloroacetic acid, cyanoacetic acid, propionic acid, butyric acid, isobutyric acid, valeric acid, isovaleric acid, pivalic acid, trifluoroacetic acid, trichloroacetic acid or acetoacetic acid, aromatic carboxylic acid-mixed acid anhydrides, e.g., mixed acid anhydrides of [II] with benzoic acid, p-toluic acid or p-chlorobenzoic acid and organic sulfonic acid-mixed acid anhydrides, e.g., mixed acid anhydrides of [II] with methanesulfonic acid, ethanesulfonic acid, benzenesulfonic acid or p-toluenesulfonic acid. Examples of the active amides are amides with nitrogen-containing heterocyclic compounds, e.g., acid amides of [II] with pyrazole, imidazole or benzotriazole and these nitrogen-containing heterocyclic compounds may have a substituent such as an alkyl group, an alkoxy group, halogen atom, an oxo group, a thioxo group or an alkylthio group. As active esters of [II], there may be used all of those which are used for synthesis of peptides. Examples thereof include, in addition to organic phosphates, e.g., diethoxy phosphate and diphenoxy phosphate, p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester and 1-hydroxy-1H-2-pyridone ester. Examples of the active thioesters of [II] include esters with aromatic heterocyclic thio compounds, e.g., 2-pyridylthiol ester and 2-benzothiazolylthiol ester and these heterocyclic rings may have a substituent such as an alkyl group, an alkoxy group, halogen atom or an alkylthio group. One to three hydroxyl groups on the benzene ring of the starting compound [II] may be protected. As examples of the protecting groups, mention may be made of substituted or unsubstituted alkanoyl groups, e.g., acetyl, propionyl and trifluoroacetyl, substituted oxycarbonyl groups, e.g., methoxycarbonyl, ethoxycarbonyl, isopropoxycarbonyl, tert-butoxycarbonyl, pehnoxycarbonyl, benzyloxycarbonyl, p-methylbenzyloxycarbonyl or benzhydryloxycarbonyl, a tert-butyl group, aralkyl groups, e.g., benzyl, p-methylbenzyl, p-methoxybenzyl, p-chlorobenzyl, benzhydryl and trityl and substituted silyl groups, e.g., trimethylsilyl and tert-butyldimethylsilyl.

The salt of the compound [III] includes salts with inorganic acids or organic acids. Examples of the inorganic acid salts of [III] include hydrochloride, hydrobromide, sulfate, nitrate and phosphate. Examples of the organic acid salts include formate, acetate, trifluoroacetate, methanesulfonate and p-toluenesulfonate.

Preparation of salts or reactive derivatives of [II] and of salts of [III] and introduction of a protecting group into [II] is easily performed by known processes or similar processes thereto. For reaction between compound [II] and compound [III], for example, a reactive derivative of starting compound [II] as a substance isolated from a reaction mixture may be allowed to react with compound [III]. Alternatively, a reaction mixture as such which contains the reactive derivative of starting compound [II] which is left unisolated may be allowed to react with compound [III]. A reaction between compound [III] and [II] which is free acid or a salt form is effected in the presence of a suitable condensation agent. The condensation agent includes, for example, N,N'-disubstituted carbodiimides such as N,N'-dicyclohexylcarbodiimide, azolides such as N,N'-carbonyldiimidazole and N,N'-thiocarbonyldiimidazole, dehydrating agents such as N-ethoxycarbonyl-2-ethoxy-1,2-dihydroquinoline, phosphorus oxychloride and alkoxyacetylene and 2-halogenopyridinium salts such as 2-chloropyridiniummethyl iodide and 2-fluoropyridiniummethyl iodide. In the case of using these condensation agents, reaction is considered to proceed through the reactive derivative of [II]. The reaction of compound [II] and compound [III] is usually carried out in a solvent. Suitable solvent is selected from those which do not harm the reaction. Examples of the solvent include ethers such as dioxane, tetrahydrofuran, diethyl ether, tert-butylmethyl ether, diisopropyl ether and ethylene glycol-dimethyl ether, esters such as ethyl formate, ethyl acetate and butyl acetate, halogenated hydrocarbons such as dichloromethane, chloroform, carbon tetrachloride, trichlene and 1,2-dichloroethane, hydrocarbons such as hexane, benzene and toluene, amides such as formamide, N,N-dimethyl-formamide and N,N-dimethylacetamide, ketones such as acetone, methyl ethyl ketone and methyl isobutyl ketone, nitriles such as acetonitrile and propionitrile and besides dimethylsulfoxide, sulforun, hexamethylphosphoroamide and water. These may be used alone or as mixed solvents. Amount of starting compound [III] used is usually 1–5 mol, preferably 1–2 mol per mol of starting compound [II].

The reaction is effected at a temperature of $-80°$–$80°$ C., preferably $-40°$–$50°$ C., most preferably $-30°$–$30°$ C. Reaction time varies depending on varieties of starting compounds [II] and [III], variety of solvent including mixing ratio in the case of mixed solvent and reaction temperature and is usually 1 minute–72 hours, preferably 15 minutes–3 hours.

In case an acid halide of [II] is used as compound [II], the reaction may be effected in the presence of a deoxidizer for removal of hydrogen halide generated from the reaction system. As the deoxidizer, mention may be made of, for example, inorganic bases such as sodium carbonate, potassium carbonate, calcium carbonate and sodium bicarbonate, tertiary amines such as triethylamine, tripropylamine, tributylamine, diisopropylethylamine, cyclohexyldimethylamine, pyridine, lutidine, γ-collidine, N,N-dimethylaniline, N-methylpiperidine, N-methylpyrrolidine and N-methylmorpholine and alkylene oxides such as propylene oxide and epichlorohydrin.

The objective compound [I] of the present invention is obtained by allowing compound [II] to react with compound [III] as mentioned above and, if necessary, elimination of the protecting group and purification. Elimination of the protecting group for hydroxyl group is effected by the process as it is which is usually employed in the field of synthesis of peptides. For example, methoxycarbonyl, ethoxycarbonyl, tert-butoxycarbonyl or phenoxycarbonyl is eliminated by acids, for example, hydrochloric acid or trifluoroacetic acid, benzyloxycarbonyl, p-methylbenzyloxycarbonyl or benzhydryloxycarbonyl is eliminated by catalytic reduction, benzyl, p-methylbenzyl, p-methoxybenzyl, p-chlorobenzyl, benzhydryl or trityl is eliminated by acids, for example, trifluoroacetic acid or catalytic reduction and trimethylsilyl or tert-butyldimethylsilyl is eliminated by water alone or in the presence of acetic acid.

When elimination of a protecting group is carried out, hydroxyl group-protected compound [I] which has been isolated from a reaction mixture obtained from the reaction of compound [II] and compound [III] may be subjected to elimination of a protecting group. Alternatively, the reaction mixture may be subjected as it is to elimination of a protecting group. Purification of the hydroxyl group-protected compound [I] or the objective compound [I] is carried out by the known methods such as extraction, gel filtration, ion-exchange resin column chromatography, silica gel thin-layer chromatography, high-performance liquid chromatography and recrystallization.

Process for production of compound [II] will be explained below. Reference is made to, for instance, preparation of compound [I] of the present invention where m is 2 and the substituent hydroxyl groups are located at 2- and 4-positions. Preparation of 2,4-dibenzyloxyphenylacetyl-L-asparagine or glutamine p-nitrophenyl ester [IIa] is explained, since it is especially useful as a starting material [II]. For instance, [IIa] is produced from 2,4-dihydroxybenzaldehyde [IV], through the route shown in the reaction formula 2.

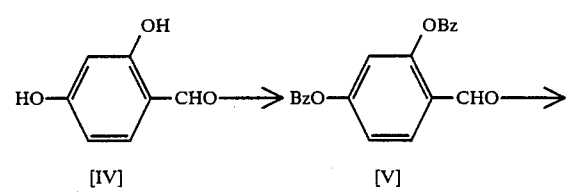

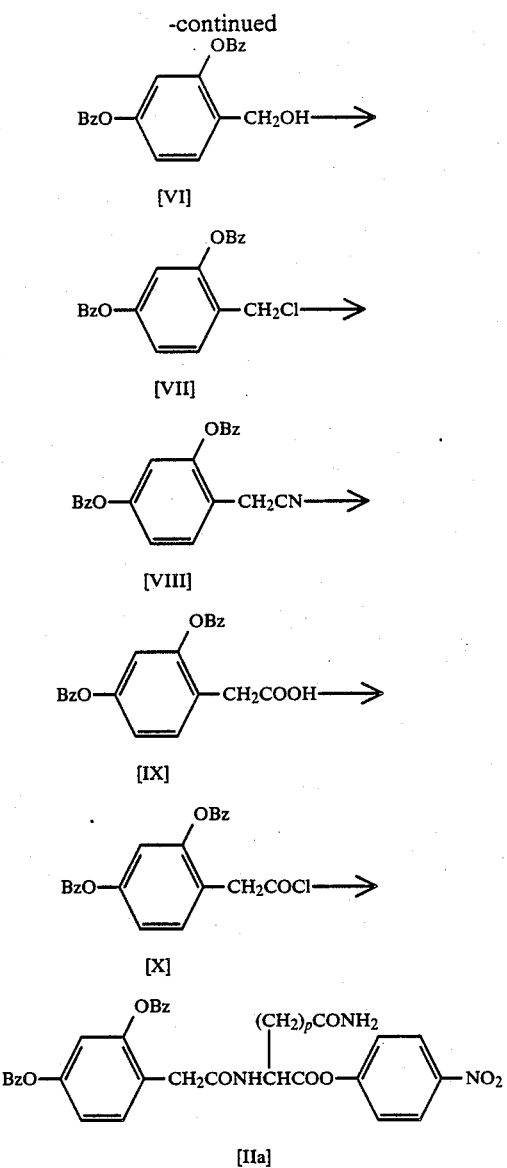

[in the above formula, Bz denotes a benzyl group]

That is, 2,4-dihydroxybenzaldehyde [IV] is benzylated with benzyl chloride to produce 2,4-dibenzyloxybenzaldehyde [V], then [V] is reduced with sodium borohydride to produce 2,4-dibenzyloxybenzyl alcohol [VI] and then, [VI] is chlorinated with thionyl chloride to produce 2,4-dibenzyloxybenzyl chloride [VII]. Then, [VII] is allowed to react with sodium cyanide to obtain 2,4-dibenzyloxyphenyl acetonitrile [VIII], thereafter [VIII] is hydrolyzed with an alkali to produce 2,4-dibenzyloxyphenylacetic acid [IX], then this [IX] is chlorinated with thionyl chloride to produce 2,4-dibenzyloxyphenylacetyl chloride [X] and further, this [X] is allowed to react with L-asparagine or glutamine p-nitrophenyl ester to obtain [IIa].

Compound [I] has glutamate receptor inhibiting activity. Therefore, compound [I] is important for research on isolation, structure elucidation and local analysis of the glutamate receptor. Further, the compound is expected to be useful for elucidation of mechanism of memory and cranial nerve diseases with which glutamic acid is associated. The inventors also confirmed that compound [I] is useful as an insecticide. That is, as explained below, a composition containing compound [I] (referred to as "composition of the present invention") has a high insecticidal activity and produces a satisfactory insecticidal effect with a low dosage. In addition to this economical advantage of low dosage, it has very low mammalian toxicity and fish toxicity and a small adverse influence to environment. Therefore, it is used effectively to control pests injurious to hygiene, animals, plants, and forests. For example, it exhibits high insecticidal activity by direct spraying to animals and plants so that it is eaten directly by or comes into direct contact with pests. That is, the compound [I] as the major ingredient of the composition of the present invention has both the safe and advantageous properties in use for pest control in agriculture.

The composition of the present invention which contains compound [I] is effective to expel or control those injurious insects belonging to Lepidoptera such as *Spodoptera litura, Plutella xylostella, Pierisrapae orucivora, Chilo suppressalis, Plusia nigrisigna, Halicoverpa assulta, Leucania separata, Mamestra brassicae, Adoxophyes orana, Syllept derogata, Cnaphalocrocis medinalis, Phthorimaea operculella, Hyphautria cunea,* and *Lymantria dispar*; those injurious insects belonging to Coleoptera such as *Epilachna vigintioctopunctata, Aulacophora femoralis, Phyllotreta striolata, Oulema orgzae, Echinocnemus squameus, Leptinotorsa decemlineata, Lissorphopterus oryzophilus,* and *Anthonomus grandis*; those injurious insects belonging to Diptera such as *Musca domestioa, Culexpipiens pallens, Cvlex pipiens molestus, Tabanus trigonus, Hylemya antiqua,* and *Hylemya platura*; those injurious insects belonging to Orthoptera such as *Locusta migratoria,* and *Gryllotalpa africana,* Blattidae and Blattellidae such as *Blatella germanica* and *Periplaneta fuliginosa*; and nematodes such as *Aphelenchoides besseyi*.

The composition of the present invention is used in the form of emulsion, oil solution, wettable powder, dust, granule, tablet, aerosol and ointment according to the intended use. To this effect, one or more of the compound [I] is dissolved or dispersed in a proper liquid carrier or mixed with or absorbed on a proper solid carrier. Preferred formulations are emulsion, wettable powder, dust and granule. These formulations may be prepared by the method known per se, if necessary, by adding an emulsifier, a suspending agent, a spreader, a penetrant, a wetting agent, a thickener and stabilizer.

Content of compound [I] in the composition of the present invention varies depending on the intended use and is suitably about 0.00001–10% by weight in the case of emulsion and wettable powder, about 0.0000001–1% by weight in the case of oil solution and dust and about 0.000001–5% by weight in the case of granule. These concentrations may be optionally changed according to the intended use. The emulsion or wettable powder is preferably diluted (for example, 100–100,000 times) with water.

The liquid carriers used in preparation of the composition of the present invention are suitably water or water soluble solvents such as alcohols (e.g., methyl alcohol, ethyl alcohol and ethylene glycol), ketones (e.g., acetone and methyl ethyl ketone) and ethers (e.g., dioxane, tetrahydrofuran and cellosolve). These solvents are used alone or as a mixture of two or more. Content of the liquid carrier in the composition of the present invention varies depending on the formulations and preferably is 5–99.99% by weight in the case of emulsion. The solid carrier includes vegetable powders (e.g., soybean powder, tobacco powder and wood powder), mineral powders (e.g., clays such as kaolin, bentonite and acid clay, talcs such as agalmatolite powder and silicas such as diatomaceous earth and mica powder), alumina, sulfur powder and active carbon. These may be used alone or as a mixture of two or more. Content of the solid carrier in the composition of the present invention varies depending on the formulations and is 90–99.999999% by weight, preferably 95–99.999999% by weight in the case of wettable powder, dust or granule.

The emulsifier, spreader, penetrant, dispersing agent, etc. contained in the insecticidal composition of the present invention are selected from surface active agents which includes soaps, polyoxyalkylaryl esters, e.g., Nonal® made by Takemoto Yushi Co., Ltd., alkyl sulfates, e.g., Emal®- 10 and Emal®- 40 made by Kao-Atlas Co., Ltd., alkyl sulfonates, e.g., Neogen® and Neogen-T® made by Dai-ichi Kogyo Seiyaku Co., Ltd.; Neopelex® made by Kao-Atlas Co., Ltd., polyoxyethylene glycol ethers, e.g., Nonipol®- 85, Nonipol®- 100, and Nonipol®- 160 made by Sanyo Kasei Co., Ltd., and polyhydric alcohol esters, e.g., Tween®- 20 and Tween®- 80 made by Kao-Atlas Co., Ltd. The amount of these surface active agents varies from one formulation to another, but 1–20% by weight, preferably 3–10% by weight, in the case of emulsion; 3–30% by weight, preferably 5–20% by weight, in the case of wettable powder; and 0–10% by weight, preferably 0.1–5% by weight, in the case of dust and granule.

The compound [I] may be used in combination with any other insecticide, e.g., pyrethrin-, organophosphate-, carbamate-, and natural-insecticides, miticide, nematicide, herbicide, plant hormone, plant growth regulator, fungicide, e.g., copper-, organochlorine-, organosulfur- and phenol-fungicides, synergist, attractant, repellent, colorant, and fertilizer in such an amount that does not impair the insecticidal activity of the compound [I].

The composition of the present invention which contains the compound [I] is used in the same manner as in the ordinary insecticidal composition. For example, it is used for seedling box treatment, foliage application, body application, water treatment and soil treatment. The dosage is varied widely depending on the timing, place and method of application and is usually 0.1 mg–10 g, preferably 1 mg–5 g in terms of active ingredient per hectare.

REFERENCE EXAMPLE

Preparation of 2,4-dibenzyloxyphenylacetyl-L-asparagine p-nitrophenyl ester [IIa-1]:

(i) 2,4-Dihydroxybenzaldehyde [IV] (14.5 g) was dissolved in ethanol (60 ml) and then thereto were added benzyl chloride (30 ml) and sodium carbonate (1.7 g), followed by reflux under heating for 5 hours. Insoluble matters were removed by filtration. The filtrate was allowed to stand for cooling and then the produced solid was collected by filtration and recrystallized from ethanol to obtain 2,4-dibenzyloxybenzaldehyde [V] (20 g, yield 60%). Melting point: 89°–90° C.

(ii) 2,4-Dibenzyloxybenzaldehyde [V] (20 g) was dissolved in methanol (700 ml) and then, thereto was added sodium borohydride (3.6 g) and this was left to stand at room temperature (20° C.) for 1.5 hour. To the reaction mixture was added water (1.5 liter) and the resulting precipitate was collected by filtration and recrystallized from ethanol to obtain 2,4-dibenzyloxybenzyl alcohol [VI] (19.8 g, yield 98%). Melting point: 84°–85° C.

(iii) 2,4-Dibenzyloxybenzyl alcohol [VI] (19.8 g) was dissolved in anhydrous benzene (150 ml) and then, thereto was added thionyl chloride (40 g), followed by reflux under heating for 1 hour. This was concentrated to dryness under reduced pressure to obtain crude 2,4-dibenzyloxybenzyl chloride [VII]. This was used for the subsequent reaction without purification.

(iv) The above obtained crude 2,4-dibenzyloxybenzyl chloride [VII] was dissolved in dimethyl sulfoxide (150 ml) and then thereto was added sodium cyanide (4 g), followed by stirring for 2 hours at room temperature (20° C.). The reaction mixture was added to water (1 liter) and extracted with dichloromethane (1 liter). The dichloromethane extract was concentrated under reduced pressure and the residue was purified by a silica gel column [inner diameter: 10 cm, length 50 cm; developer: dichloromethane-hexane 1:1 (v/v) mixed solution] and furthermore, was recrystallized from diethyl ether-hexane 2:1 (v/v) mixed solution to obtain 2,4-dibenzyloxyphenylacetonitrile [VIII] (14.3 g, yield from [VI]: 70%). Melting point: 99°–100° C.

(v) 2,4-Dibenzyloxyphenylacetonitrile [VIII] (14.3 g) was dissolved in ethanol (250 ml) and then, thereto was added an aqueous potassium hydroxide solution (prepared by dissolving 32 g of potassium hydroxide in 80 ml of water), followed by reflux under heating for 15 hours. The reaction mixture was concentrated under reduced pressure and then dissolved in water (100 ml). The solution was made acidic with concentrated hydrochloric acid and extracted with dichloromethane. The dichloromethane extract was dried over anhydrous magnesium sulfate and concentrated under reduced pressure. Thereafter, the residue was subjected to separation and purification by a silica gel column [inner diameter: 10 cm, length: 50 cm; developer: dichloromethane-ethyl acetate 4:1 (v/v) mixed solution]. Thus separated and purified product was recrystallized from benzene to obtain 2,4-dibenzyloxyphenylacetic acid [IX] (14.4 g, yield 95%). Melting point: 139° C.

(vi) 2,4-Dibenzyloxyphenylacetic acid [IX] (1.4 g) was dissolved in anhydrous benzene (30 ml) and (vi) 2,4-Dibenzyloxyphenylacetic acid [IX] (1.4 g) was dissolved in anhydrous benzene (30 ml) and then thereto was added thionyl chloride (5 g) and the mixture was left to stand at room temperature (20° C.) for 20 minutes. The reaction mixture was concentrated to dryness under reduced pressure to obtain crude 2,4-dibenzyloxyphenylacetyl chloride [X]. This was used for the subsequent reaction without purification.

(vii) The above obtained crude 2,4-dibenzyloxyphenylacetyl chloride [X] was dissolved in anhydrous N,N-dimethylformamide (20 ml) and then thereto was added a solution of L-asparagine p-nitrophenyl ester trifluoroacetate in anhydrous N,N-dimethylformamide [prepared by treating N-(p-methoxybenzyloxycarbonyl)-L-asparagine p-nitrophenyl ester (1.6 g) with trifluoroacetic acid (3 ml) in the presence of anisole (1.2 g) at 0° C. for 1 hour, concentrating the treated product to dryness under reduced pressure and dissolving the residue in anhydrous N,N-dimethylformamide (20 ml)]. Thereto was further added triethylamine (1.8 ml), followed by concentrating under reduced pressure at 40°

C. or lower. The residue was subjected to separation and purification by a silica gel column (inner diameter: 5 cm, length: 30 cm; developer: ethyl acetate) to obtain 2,4-dibenzyloxyphenylacetyl-L-asparagine p-nitrophenyl ester [IIa-1] (290 mg, yield from [IX] 13%).

EXAMPLE 1

Production of 2,4-dihydroxyphenylacetyl-L-asparaginyl-cadaverine [Ia] (compound No. 3 in Table 1)

(i) 2,4-Dibenzyloxyphenylacetyl-L-asparagine p-nitrophenyl ester [IIa-1] (40 mg) was dissolved in anhydrous N,N-dimethylformamide (2 ml). This solution was added to a solution of cadaverine (1,5-diaminopentane, 80 mg) in anhydrous N,N-dimethylformamide (1 ml).

Thereto were further added 5% aqueous sodium bicarbonate solution (5 µl) and then water (30 ml). The resulting precipitate was collected by filtration and then well washed with water and dried to obtain 2,4-dibenzyloxyphenylacetyl-L-asparaginyl-cadaverine (34 mg, yield 92%). This gave a single spot on thin layer chromatograph and single peak on high-performance liquid chromatograph.

(ii) The above 2,4-dibenzyloxyphenylacetyl-L-asparaginylcadaverine (34 mg) was dissolved in acetic acid (1 ml) and the solution was subjected to catalytic reduction in the presence of 10% palladium-carbon (15 mg) for 3 hours in a hydrogen atmosphere. After the reaction, the catalyst was removed by filtration and the filtrate was concentrated to dryness under reduced pressure. The residue was subjected to separation and purification by a high-performance liquid chromatography [reversed-phase partition column TSK gel ODS-120T manufactured by Toyo Soda Mfg., Co., Ltd.; inner diameter of the column: 46 mm, length: 250 mm; resin diameter: 5 µm; column temperature: 40° C.; eluent: mixed solvent of 0.02% hydrochloric acid and acetonitrile 3:7 (v/v)]. The solvent was distilled off to obtain hydrochloride of 2,4dihydroxyphenylacetyl-L-asparaginylcadaverine [Ia] (7.5 mg, yield 30%).

Proton NMR of Ia-hydrochloride (400 MHz, $D_2O$, ppm): 1.09(quin., 2H), 1.31(quin., 2H), 1.42(quin., 2H), 2.55(dd, 6.4 Hz, 13 Hz, 1H), 2.60(dd, 6.4 Hz, 13 Hz, 1H), 2.72(dt-like, 2H), 3.00(ddt, 1H), 3.06(ddt, 1H), 3.32(d, 15 Hz, 1H), 3.39(d, 15 Hz, 1H), 4.43(dd, 1H), 6.30(s-like, 2H), 6.94(m, 1H).

EXAMPLE 2

Production of 2,4-dihydroxyphenylacetyl-L-asparaginyl-spermine [Ib] (compound No. 28 in Table 1):

(i) 2,4-Dibenzyloxyphenylacetyl-L-asparagine p-nitrophenyl ester [IIa-1] (40 mg) was dissolved in anhydrous N,N-dimethylformamide (2 ml) and then, this solution was added to a solution of spermine (1,4 bis [{(3-amino)propyl}amino]butane, 144 mg) in anhydrous N,N-dimethylformamide (1 ml).

Further, thereto were added 5% aqueous sodium bicarbonate solution (5 µl) and then water (30 ml). Resulting precipitate was collected by filtration and well washed with water and dried to obtain 2,4-dibenzyloxyphenylacetyl-L-asparaginylspermine (40 mg, yield 90%). This gave single spot on a thin layer chromatograph and single peak on high-performance liquid chromatograph.

(ii) The above 2,4-dibenzyloxyphenylacetyl-L-asparaginylspermine (40 mg) was dissolved in acetic acid (1 ml) and the solution was subjected to catalytic reduction in the presence of 10% palladium-carbon (15 ml) in hydrogen atmosphere for 3 hours. After the reaction, the catalyst was removed by filtration and the filtrate was concentrated to dryness under reduced pressure. The residue was subjected to separation and purification by a high-performance liquid chromatography [reversed-phase partition column TSK gel ODS-120T manufactured by Toyo Soda Mfg., Co., Ltd.; inner diameter: 46 mm; length: 250 mm; resin diameter: 5 µm; column temperature: 40° C.; eluent: a mixed solvent of 0.02% hydrochloric acid and acetonitrile 7:3 (v/v)]. The solvent was distilled off to obtain trihydrochloride of 2,4-dihydroxyphenylacetyl-L-asparaginylspermine [Ib] (15.5 mg, yield 54%).

Proton NMR of the Ib-trihydrochloride (400 MHz, $D_2O$. ppm): 1.56(quin., 4H), 1.69(quin., 2H), 1.92(quin., 2H), 2.59(dd, 7 Hz, 17 Hz, 1H), 2.62(dd, 7 Hz, 17 Hz, 1H), 2.76(t, 2H), 2.77(t, 2H), 2.92(t, 2H), 2.95(t, 2H), 2.98(t, 2H), 3.11(ddt, 1H), 3.18(ddt, 1H), 3.35(d, 15 Hz, 1H), 3.41(d, 15 Hz, 1H), 4.42(t, 7 Hz, 1H), 6.30(s-like, 2H), 6.92(m, 1H).

EXAMPLE 3

Production of N-(2,4-dihydroxyphenylacetyl-L-asparaginyl)N'-ethyl cadaverine [Ic] (compound No. 6 in Table 1):

(i) 5-Amino-1-pentanol (5.15 g) was dissolved in water-methanol (1:1, 100 ml) and acetic anhydride (5.1 g) was added dropwise to the solution under stirring. After the solution was stirred for one hour, the solvent and acetic acid produced were distilled off completely. An oily material obtained was dissolved in anhydrous tetrahydrofuran (100 ml) and then lithium aluminum hydride (0.37 g) was added thereto. Heating was made for one hour under refluxing, and leaving to stand until the mixture was cooled.

Excess reducing agent was decomposed with ethyl acetate. An insoluble substance produced was separated by filtration and the filtrate was concentrated to obtain 5-(N-ethylamino)-1-pentanol (3.6 g).

(ii) To solution (70 ml) of 5-(N-ethylamino)-1-pentanol (3.6 g) in dioxane were added di-tert. butyl dicarbonate (6.6 g) and triethylamine (2.7 g) and stirring was made for one hour under ice cooling. After a solvent was distilled off, ethyl acetate was added to the residue until the solid material was completely dissolved.

The ethyl acetate solution was washed with aqueous potassium hydrogensulfate solution (10%). After an organic layer was dried over sodium sulfate, the solvent was distilled off to obtain 5-(N-tert-butyloxycarbonyl, N-ethylamino)-1-pentanol (4.7 g).

(iii) To solution (60 ml) of 5-(N-tert.butyloxycarbonyl, N-ethylamino)-1-pentanol (4.7 g) in anhydrous tetrahydrofuran were added triphenylphosphine (7.8 g) and phthalimide (4.4 g). To the solution was added dropwise dimethyl azodicarboxylate (5.2 g) with stirring under ice cooling. After stirring was made for one hour, the solvent was distilled off under reduced pressure. The residue was extracted with n-hexane-ethyl acetate (2:1). Solution extracted was washed with water and the solvent was distilled off to obtain N-[5-(N-tert.butyloxycarbonyl, N-ethylamino)] pentylphthalimide (4.2 g).

(iv) To solution of N-[5-(N-tert.butyloxycarbonyl, N-ethylamino)] pentylphthalimide (4.2 g) in ethanol was added hydrazine monohydride (3.4 g) and the mixture was heated up to 70° C. for 1.5 hours. After crystal produced was filtered, the filtrate was concentrated under reduced pressure. To an oily material obtained was added diethylether-ethyl acetate (1:1, 20 ml) and a crystal produced was removed by filtration. The filtrate was concentrated under reduced pressure to obtain 5-(N-tert.butyloxycarbonyl, N-ethylamino)-1-aminopentane (2.4 g).

(v) To solution (2 ml) of 2,4-dibenzyloxyphenylacetyl-L-asparagine p-nitrophenyl ester (80 mg) in anhydrous N,N-dimethylformamide was added solution (1 ml) of 5-(N-tert.butyloxycarbonyl, N-ethylamino)-1-aminopenthane (120 mg) in anhydrous N,N-dimethylformamide. Isolation was effected in accordance with the procedure in Example 1, (i) to obtain N-(2,4-benzyloxyphenylacetyl-L-asparaginyl), N'-tert.butyloxycarbonyl, N'-ethylcadaverine (67 mg).

(vi) N-(2,4-dibenzyloxyphenylacetyl-L-asparaginyl, N'-tert.butyloxycarbonyl, N'-ethylcadaverine (67 mg) was dissolved in trifluoroacetic acid (1 ml). After 10 minutes, trifluoroacetic acid was distilled off under reduced pressure. After the residue obtained was dissolved in acetic acid (1 ml), catalytic reduction was effected for 3 hours under a hydrogen gas atmosphere in the presence of 10% palladium-carbon (15 mg).

Isolation and purification were conducted in the same manner as in Example 1, (ii) until N-(2,4-dihydroxyphenylacetyl-L-asparaginyl), N'-ethylcadaverine [1c] hydrochloride was obtained.

| SIMS m/z: | 395 [M$^+$ + H$^+$] |
|---|---|
| (C$_{19}$H$_{30}$N$_4$O$_5$: | M = 394) |

EXAMPLE 4

Production of N-[3-N-(2,4-dihydroxyphenylacetyl-L-asparaginyl)aminopropyl], N'-(3-N-ethylaminopropyl)-1,4-butanediamine (Id, compound No. 55 in Table 1):

(i) To solution (2 ml) of 2,4-dibenzyloxyphenylacetyl-L-asparagine p-nitrophenyl ester (40 mg) in N,N-dimethylformamide was added solution (1 ml) of N-(3-N-ethylaminopropyl), N'-(3-aminopropyl)-1,4-butanediamine (160 mg) in anhydrous N,N'-dimethylformamide. Stirring was made at room temperature for 10 minutes.

The same procedure as in Example 2, (i) was applied to thereafter and isolation and purification gave N-[3-N-(2,4-dibenzyloxyphenylacetyl-L-asparaginyl)aminopropyl], N'-(3-N-ethylaminopropyl)-1,4-butanediamine (34 mg).

(ii) Solution (1 ml) of N-[3-N-(2,4-dibenzyloxyphenylacetyl-L-asparaginyl)aminopropyl], N'-(3-N-ethylaminopropyl)-1,4-butanediamine (34 mg) in acetic acid was subjected to catalytic reduction for 3 hours under a hydrogen gas atmosphere in the presence of 10% palladium-carbon (20 mg). The same procedure as in Example 2, (i), the latter half was applied to until N-[3-N-(2,4-dihydroxyphenylacetyl-L-asparaginyl)aminopropyl], . N'-(3-N-ethylaminopropyl)-1,4-butanediamine hydrochloride (17.3 mg) was obtained.

| SIMS m/z: | 495 [M$^+$ + H$^+$] |
|---|---|
| (C$_{24}$H$_{42}$N$_6$O$_5$: | M = 494) |

EXAMPLE 5

(wettable powder)

| Compound Ia-hydrochloride | 0.001 wt % |
|---|---|
| Sodium lignin sulfonate | 9.999 wt % |
| Nonipol ® - 85 | 10 wt % |
| Clay | 80 wt % |

The above components were mixed to obtain a wettable powder.

EXAMPLE 6

(dust)

| Compound Ia-hydrochloride | 0.0001 wt % |
|---|---|
| Clay | 99.9999 wt % |

The above were homogenously mixed to obtain a dust.

EXAMPLE 7

(wettable powder)

| Compound Ib-trihydrochloride | 0.001 wt % |
|---|---|
| Sodium lignosulfonate | 9.999 wt % |
| Nonipol ® - 85 | 10 wt % |
| Clay | 80 wt % |

The above were mixed to obtain a wettable powder.

EXAMPLE 8

(dust)

| Compound Ib-trichloride | 0.0001 wt % |
|---|---|
| Clay | 99.9999 wt % |

The above were homogenously mixed to obtain a dust.

TEST EXAMPLE

Five young larvae of *Culex pipiens molestus* were placed in a glass test tube, 6 mm in diameter, containing 0.2 ml of aqueous solution of the compound Ia-hydrochloride or trihydrochloride in a concentration of 50 μg/ml. Three hours later, the number of poisoned and dead larvae was counted. This test was duplicated. The results are shown below. As a control, the sample solution was replaced by 0.2 ml of water in place of 0.2 ml of aqueous solution of compound Ia-hydrochloride or Ib-trihydrochloride in a concentration of 50 μg/ml.

| Ratio of poisoned + dead larvae (%) | |
|---|---|
| Ib | 10 |
| Control | 0 |

What is claimed is:

1. A compound of the formula:

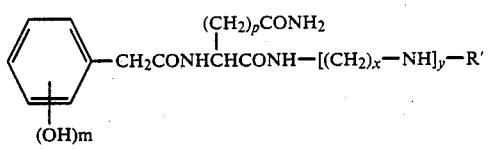

wherein R' is hydrogen atom of an alkyl containing 1 to 10 carbon atoms group, m is an integer of 1 to 3, p is an integer of 1 to 2, x is an integer of 2 to 6 and y is an integer of 1 to 3 or a salt thereof.

2. A compound or a salt thereof according to claim 1, wherein R' is hydrogen atom and y is 1.

3. A compound or a salt thereof according to claim 1, wherein R' is the alkyl group and y is 1.

4. A compound or a salt thereof according to claim 1, wherein R' is hydrogen atom and y is 2.

5. A compound or a salt thereof according to claim 1, wherein R' is the alkyl group, and y is 2.

6. A compound or a salt thereof according to claim 1 wherein R' is hydrogen atom and y is 3.

7. A compound or a salt thereof according to claim 1 wherein R' is the alkyl group and y is 3.

8. A compound or a salt thereof according to claim 1 or 2 wherein m is 2, the substituent hydroxyl group is located at 2 and 4 positions, p is 1 and $-[(CH_2)_x-NH]_y-R'$ is $-(CH_2)_5NH_2$.

9. A compound or a salt thereof according to claim 1 or 6 wherein m is 2, the substituent hydroxyl group is located at 2 and 4 positions, p is 1 and $-[(CH_2)_x-NH]_y-R'$ is $-(CH_2)_3NH(CH_2)_4NH(CH_2)_3NH_2$.

10. A compound or a salt thereof according to claim 1 or 3 wherein m is 2, the substituent hydroxyl group is located at 2 and 4 positions, p is 1 and $-[(CH_2)_x-NH]_y-R'$ is $-(CH_2)_5NHC_2H_5$.

11. A compound or a salt thereof according to claim 1 or 7 wherein m is 2, the substituent hydroxyl group is located at 2 and 4 positions, p is 1 and $-[(CH_2)_x-NH]_y-R'$ is $-(CH_2)_3NH(CH_2)_4NH(CH_2)NHC_2H_5$.

12. A compound or a salt thereof according to claim 1, wherein R' is an alkyl group containing from 1 to 6 carbon atoms.

13. An insecticidal composition containing an effective amount of a compound of the formula:

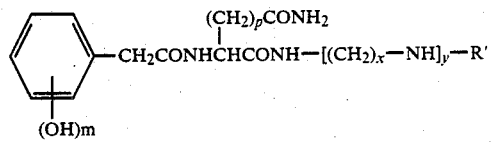

wherein R' is hydrogen atom or an alkyl group containing 1 to 10 carbon atoms, m is an integer of 1 to 3, p is 1 or 2, x is an integer of 2 to 6 and y is an integer of 1 to 3, or a salt thereof in the presence of a carrier.

14. An insecticidal composition according to claim 13, wherein R' is an alkyl group containing 1 to 6 carbon atoms.

* * * * *

UNITED STATES PATENT AND TRADEMARK OFFICE
CERTIFICATE OF CORRECTION

PATENT NO. : 4,918,107
DATED      : April 17, 1990
INVENTOR(S) : T. NAKAJIMA, et al It is certified that error appears in the above-identified patent and that said Letters Patent is hereby corrected as shown below:

Column 31, line 9, after "atom",
   "of" should read --or-- and after "alkyl"
   insert --group--

Column 31, line 10, delete "group".

Signed and Sealed this

Twenty-second Day of October, 1991

Attest:

HARRY F. MANBECK, JR.

*Attesting Officer*   *Commissioner of Patents and Trademarks*